United States Patent [19]
Devitt et al.

[11] Patent Number: 5,374,122
[45] Date of Patent: Dec. 20, 1994

[54] METHOD FOR QUANTIFYING POROSITY OF PARTS OF SIMPLE AND COMPLEX GEOMETRIES

[75] Inventors: John W. Devitt, Loveland; Eric A. Anderson, Hamilton, both of Ohio

[73] Assignee: The United States of America as represented by the Secretary of the Air Force, Washington, D.C.

[21] Appl. No.: 10,953

[22] Filed: Jan. 29, 1993

[51] Int. Cl.$^5$ .................. G01N 25/00; G01N 15/08
[52] U.S. Cl. ........................ 374/45; 374/153; 73/38
[58] Field of Search ............... 374/45, 153; 73/38

[56] References Cited

U.S. PATENT DOCUMENTS

| | | | |
|---|---|---|---|
| 3,939,698 | 2/1976 | De Lacy | 374/45 |
| 4,236,403 | 12/1980 | Poppendiek | 374/44 |
| 4,453,398 | 6/1984 | Demirel et al. | 374/45 |
| 4,623,263 | 11/1986 | Barberi et al. | 73/38 |
| 4,640,627 | 2/1987 | Tracy et al. | 374/121 |
| 4,817,020 | 3/1989 | Chande et al. | 364/557 |
| 4,818,102 | 4/1989 | Glenn | 356/43 |
| 4,840,496 | 6/1989 | Elleman et al. | 374/124 |
| 4,928,254 | 5/1990 | Knudsen et al. | 374/44 |
| 5,001,657 | 3/1991 | Yagura et al. | 364/557 |
| 5,044,767 | 9/1991 | Gustafsson | 374/44 |
| 5,159,569 | 10/1992 | Xu et al. | 374/45 |

FOREIGN PATENT DOCUMENTS 1659786 6/1991 U.S.S.R. ................... 374/45

OTHER PUBLICATIONS

Somerton, W., "Some Thermal Characteristics of Porous Rocks," Petroleum Transactions, AIME, pp. 375-378 (1958).

Primary Examiner—Diego F. F. Gutierrez
Attorney, Agent, or Firm—Donald J. Singer; Thomas C. Stover

[57] ABSTRACT

A method and apparatus for inspecting nonmetallic parts, including composite parts for, e.g. aircraft engines by quantifying their porosity, wherein a laser beam is directed to one side of the part to heat a portion thereof, with a delay being noted for the applied heat to transmit through said part to the opposite side thereof. An infrared radiometer (IR) is mounted to view such opposite side and to read (after such delay) the heat transmitted therethrough in the form of voltage (increase) readings. Such IR readings are taken at points across the part being inspected and the readings are then compared to a known data base of temperature change against vol. % porosity or the resulting calibrated porosity curve, to quantify the % porosity at various points on the sample. The inventive method can read or quantify porosity parts of simple geometry as well as of complex geometry, including engine housing flanges of small radii of curvature.

13 Claims, 2 Drawing Sheets

METHOD FOR QUANTIFYING POROSITY OF PARTS OF SIMPLE AND COMPLEX GEOMETRIES

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to a method for quantifying porosity of parts, particularly parts of simple and complex geometries.

2. The Prior Art

In the fabrication of parts, e.g., metal or composite parts, it is often important to know the porosity thereof as the more porous parts are lighter and structurally weaker, while the less porous parts are heavier, stronger, and more thermally conductive. While more porous parts have their uses e.g., in lightweight or insulative structures, excess porosity is a detriment in aircraft engines, including gas turbine engines. Accordingly, it is important to have a reliable method for quantifying the porosity of parts in various structures, e.g. in gas turbine engines.

Prior art inspection methods can quantify porosity in parts of relatively simple geometry. Thus, ultrasonic methods which employ a part-contacting probe or a microfocus x-ray method can quantify porosity on flat walled parts and e.g. cylinder walls but cannot accurately guage complicated geometries. These complicated geometries include parts of small, tight, or decreasing radii such as the curved flange at the end of a gas turbine engine housing. An example of such housing is shown as housing 10 in FIG. 2 with its cylindrical walls 12 and end flange 14 of small and changing radii of curvature. Accordingly it is important to quantify the porosity both at engine housing wall 12 and curved flange 14 for accurate inspection thereof.

In other prior art, Japanese patent 63-58242 (1988) directs a focused laser beam at a sample to measure the thermal-diffusivity thereof using a quadratic equation. There is also Soviet patent 873087 (1981) which applies heat to a sample and compares the temperature change on both sides of such sample to obtain the coefficient of heat conductivity thereof. Then there is Soviet patent 1318886 (1987) which discloses applying a pulse heating source to a sample and records the temperature increase to the reverse side thereof for monitoring of thermal conductivity.

None of the above references suggests measuring or quantifying the porosity of a sample whether of simple or complex geometry.

However, as noted above, there is a need and market for accurately measuring or quantifying the porosity of non metallic parts including composite parts of complex geometry, which method substantially overcomes the above prior art shortcomings.

There has now been discovered a method which quantifies the porosity of a non metallic part including a composite part of simple or complex geometry, without damaging or contacting such part, to the end that such part can be accurately inspected for use or non-use.

SUMMARY OF THE INVENTION

Broadly the present invention provides a method for quantifying porosity in non metallic parts comprising, a) directing a laser beam to one side of the part to heat at least a portion thereof, b) monitoring the part on an opposite side thereof with an infrared radiometer to read the heat transmitted therethrough and c) comparing the thermal infrared levels obtained on the opposite side of the part, with a known data base of such levels from calibrated porosity samples or a curve thereof, to quantify the porosity at at least one point on the reverse side of the sample.

By "quantifying" as used herein, is meant measuring or accumulating data of the porosity of a sample at one or more points thereof.

By "non metallic parts" as used herein, is meant parts of little or no metal content such as of ceramics, composites, inoganics, organics, polymers, cellulose or a combination thereof and the like.

By "composites" as used herein is meant a material in which two or more structurally complementary components are mixed to produce a material having at least one structural or functional property or improvement thereof, not present or beyond that found, in any of the indivdual components An example of a composite part is one made of a woven mesh of carbon fibers imbedded in a plastic, e.g. a thermoset plastic.

BRIEF DESCRIPTION OF THE DRAWINGS

The invention will become more apparent from the following detailed specification and drawings in which.

DESCRIPTION OF PREFERRED EMBODIMENTS

Figure 1:
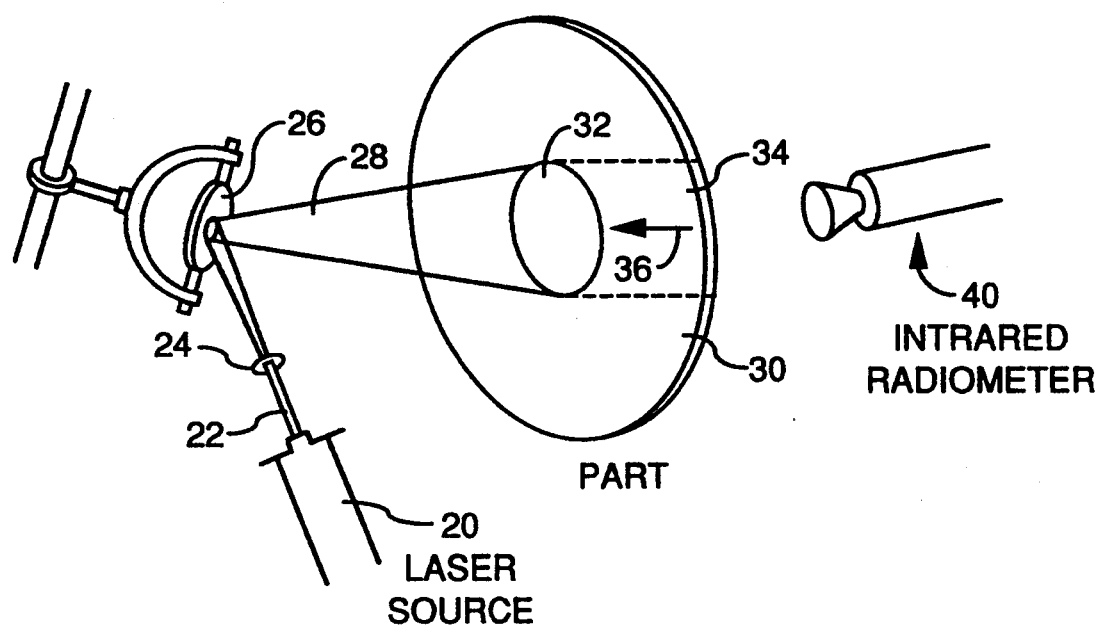
FIG. 1 is fragmentary schematic perspective view of an apparatus embodying the measurement of porosity in a sample according to the present invention.

Referring now in more detail to the drawings, laser emitter 20 directs its beam 22 through a divergent lens 24 to pivotable mirror 26, which directs the expanding laser beam 28 to part 30 of simple geometry, as shown in FIG. 1. The mirror 26 pivots so as to move the laser spot 32 across the part 30, in a path 34, in the direction of arrow 36, as shown in FIG. 1. The sample 30 is monitored on its reverse side, by infrared radiometer(IR) 40 which pivots in delayed tracking of the spot 32 as it moves across the sample 30, i.e. lags behind such spot to allow time for heat from the laser beam 28 to penetrate the sample 30 to the reverse side thereof, for heat penetration data, as indicated in FIG. 1. Such delayed tracking of the heat spot 32 in the sample 30 by the IR 40, yields more accurate heat penetration and thus porosity data than concurrent tracking of such spot would do.

Figure 2:
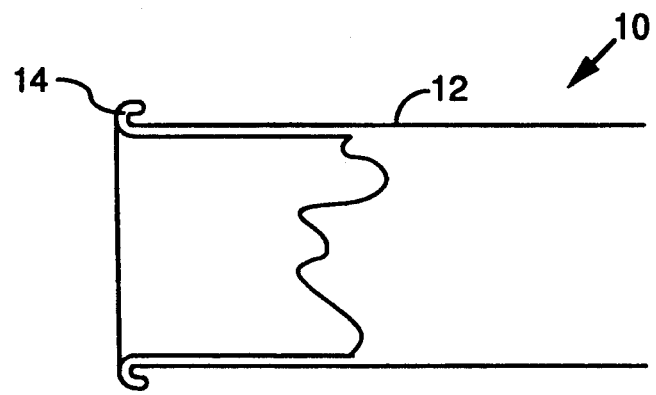
FIG. 2 is a fragmentary sectional elevation view of a part to be inspected for porosity per the invention.

The porosity measuring embodiment shown in FIG. 1 can readily quantify porosity in parts of simple geometry, e.g. the cylindrical walls 12 of engine housing 10, shown in FIG. 2.

In the method of the invention illustrated in FIG. 1 (and also in FIG. 3, discussed below), the part is heated with laser radiation while viewed from the opposite side with a high resolution IR. The heat transmitted through the part will be affected by the porosity of the material, with non porous material being a better conductor of heat. The laser heating burst is precisely controlled by computer to achieve repeatable results. After heating data is acquired from the IR at a specified time interval, again under computer control, to ensure accuracy and repeatability of the measured data. The thermal infrared levels obtained in each case are then compared to a known data base of such levels from calibrated porosity samples. The unknown part can then have its porosity quantified by the use of the calibration curve from the known sample, an example of which curve is shown in FIG. 4 hereof.

Figure 4:
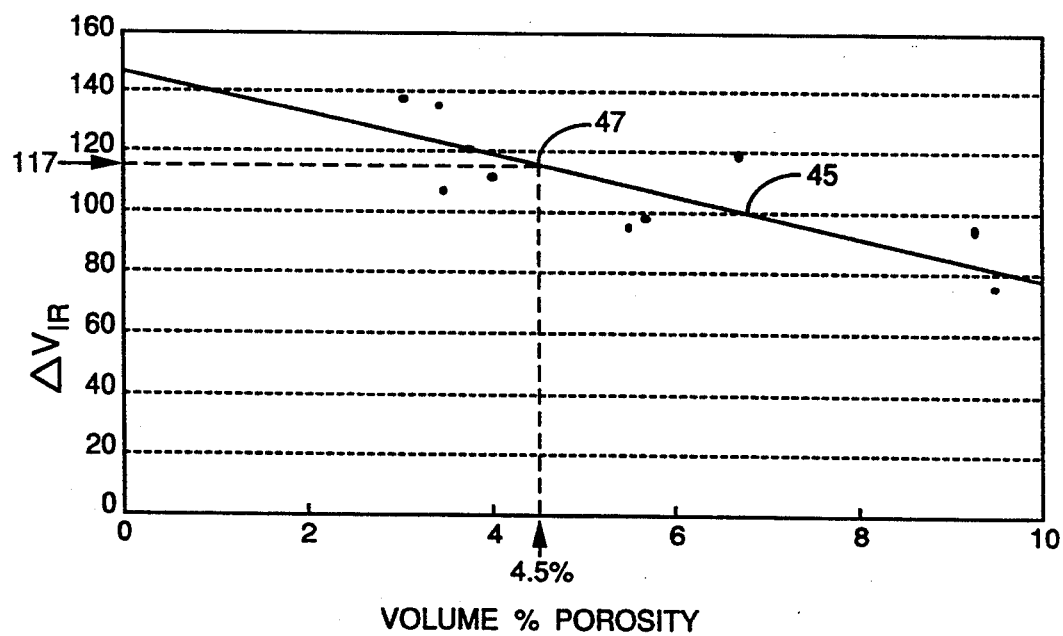

In the curve of FIG. 4, the x axis is a measure of porosity by volume in the sample, e.g. from 0 to 10 vol. %. The y axis notes the change in voltage generated by the IR ($\Delta V_{IR}$), which equates to the change in temperature from the unheated to the heated part, on the reverse side thereof, which is noted on such y axis as $\Delta V_{IR}$.

For example, if in FIG. 1 the IR 40 notes a voltage rise in the heated sample 30 of 117 V, then, reading across from 117 V on the y axis to a point 47 on the curve 45 of FIG. 4 and then at a point on the x axis directly below, one reads that the porosity of such sample at the testing point or area is 4.5 vol. % porosity. Thus numerous measurements across a sample can be taken to readily determine the porosity thereof utilizing a calibrated curve such as curve 45 of FIG. 4.

Advantages of the diverging laser beam scanning method of the invention shown in FIG. 1, include heating and testing a relatively wide field of view, e.g. path 34 of FIG. 1, while maintaining high resolution and accurate data output from IR 40, shown in FIG. 1. Also the method employing the invention of FIG. 1 is relatively quick and inexpensive to perform, is a non-contact method, non-damaging to the sample and is highly suitable for automation.

However for quantifying porosity of parts of more complex geometry, e.g. parts of small radii of curvature such as the flange 14 of the engine housing 10 of FIG. 2, another embodiment of the invention is employed. Such embodiment is employed, e.g. in measuring the engine flange 14 of engine housing 10, as shown in FIGS. 3 and 2.

Figure 3:
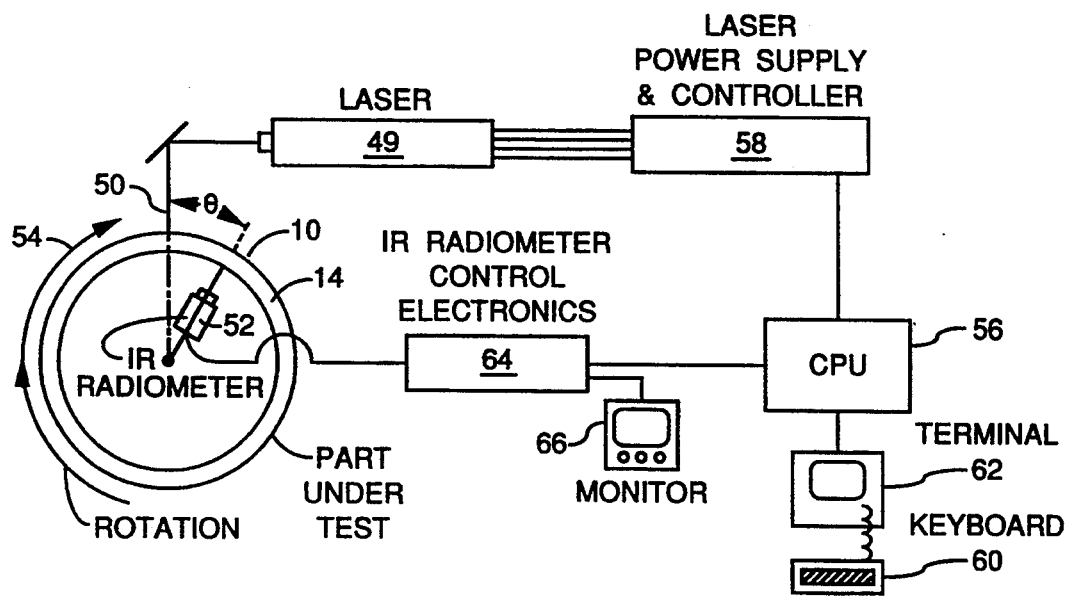
FIG. 3 is a schematic block diagram of another porosity measuring method according to the present invention and FIG. 4 is a calibration curve of porosity data for use with a method of the invention.

Thus for flange radii areas on rounded including cylindrical parts, scanning of the radius area of flange 14 of FIG. 3, can be accomplished by axially rotating the part (engine housing 10) at a fixed rate, with a laser beam 50 of a laser gun 49, impinging on one side of the sample and an IR 52 being positioned to view or monitor the other side of the flange 14. However the IR 52 is offset from incoming laser beam (on the other side of the flange 14) by a desired angular displacement, dependent on a) the desired time delay between heating of the flange 14 on one side and data acquisition of the heat transmitted through such flange (as affected by the porosity thereof) and b) the rate of rotation of such flange 14, as shown or indicated in FIG. 3 hereof.

The engine housing 10 and its flange 14 are rotated in the example of FIG. 3, clockwise as indicated by arrow 54 thereof. The IR 52 is offset from the incoming laser beam 50 by an angle $\theta$ as shown in such Figure. The laser beam 50 can be a continuous beam or in controlled bursts or pulses thereof, as controlled by the computer 56, power supply 58 and laser gun 49, as shown in FIG. 3. The CPU or computer 56 is programmed in turn, by an operator (not shown) at key board 60, viewing monitor 66 and terminal 62, as shown in FIG. 3.

The IR 52 is also controlled by the computer 56 and the electronic control box 64. The infrared images of the reverse side of the heated part are shown on the monitor 66 to, e.g. the operator of keyboard 60, who (upon inspection of such images), can pass or reject a part for, e.g. a crack or excess porosity. The operator of keyboard 60 can also regulate the components of the porosity measuring circuit of FIG. 3, as desired per the invention. Thus the computer 56, as directed by the operator of the keyboard 60, can change the intensity of the laser beam 50, the speed of rotation of the engine flange 14 and/or the offset angle of the IR 52, to optimize the porosity data obtained on the flange 14 and to input such data back to the computer 56 for read-out or print-out purposes. Such porosity data in the form of $\Delta V_{IR}$, can be read against the porosity calibration curve of FIG. 4, to determine the porosity of various portions of such of the part, i.e. such flange 14 or other part of small radius or otherwise complex geometry.

Refering again to FIG. 3, the IR 52 is offset from the incoming laser beam 50, to give time for the heat from such laser beam to work its way through the rotating housing flange 14, while the so-heated flange spot is rotating toward the IR 52 field of view, as indicated in FIG. 3. Thus a) heating, b) delay for heat transmittal through the part and c) observation by the IR, all occur on different sections of the part simultaneously, to result in considerable time savings and increased data flow on such rotating parts.

The following example is given in illustration of a porosity quantification method embodying the invention and should not be construed in limitation thereof.

EXAMPLE I

Several calibrated porosity composite parts were obtained for this example. The samples were of a composite material of woven graphite mesh imbeded in a thermoset plastic, sold commercially in the U.S. as "PMR-15". The samples were sized about 2 in. by 3 in. by ¼ in. The porosity ranged from 2.7 to 9.5 vol. %, the region of interest. An Nd:YAG laser at 1.06 μm was used to heat the part under test from one direction. A nine second burst at 12 W was used in this example. The part was observed on its opposite side, with an inframetrics 210 IR camera operating in the 8–12 μm band. The data were recorded after a six second time lag after the heating pulse was stopped. The results were as follows.

TABLE I

| SAMPLE | START V (volts) | FINISH V | $\Delta V_{IR}$ | POROSITY vol. % |
|---|---|---|---|---|
| 6293-6 | 31 | 202 | 171 | 2.7 |
| 6294-0 | 18 | 156 | 138 | 3.25 |
| 6294-1 | 19 | 123 | 104 | 3.50 |
| 6293-2 | 23 | 160 | 137 | 3.85 |
| 6294-5 | 21 | 140 | 119 | 3.3–4.4 |
| 6294-6 | 29 | 129 | 105 | 3.8–9.5 |
| 6293-0 | 29 | 166 | 137 | 5.33 |
| 6294-3 | 24 | 106 | 82 | 5.68 |
| 6294-2 | 27 | 113 | 86 | 5.7–6.6 |
| 6293-3 | 29 | 146 | 117 | 6.3–7.1 |
| 6293-4 | 24 | 114 | 90 | 9.0–9.5 |
| 6293-5 | 27 | 101 | 74 | 9.1–10.2 |

The last two columns of the above data is plotted as the previously noted curve 45 of FIG. 4.

The above Example establishes a clear relationship between the porosity level and the measured difference in the infrared value of each sample. Thus per the tabulated data, as the change in the infrared value ($\Delta V_{IR}$) decreases, the porosity increases, e.g. comparing samples 6293-6 and 6294-5.

The proposed methodology for aircraft engine components and other non metallic parts is to utilize a rotating stage and an angular offset between the laser spot and the IR. This provides a fixed delay for the applied heat to transmit through the sample to the other side for observation thereof, while allowing heating, delay and observation to occur on different sections of the part simultaneously for a significant time savings in part testing as indicated above.

Accordingly applicants' inventive method provides for quantifying or measuring the porosity in simple parts e.g., the sidewalls of engine housings as well as parts of complex geometry such as an engine housing flange of small radii of curvature.

While heating of the part tested for porosity is desirably by laser beam, e.g. per FIGS. 1 and 3, such heating can also be accomplished by other heating means, including hot air jet or hot gas jet and the like, assuming the uniform application of heat in pulse or continuous form.

What is claimed is:

1. A method for quantifying porosity of a non-metallic part having a first side and a second side substantially opposite said first side comprising:
    a) applying heat to said first side by a gas jet or laser beam which relatively moves as a heating spot across a portion of said first side,
    b) viewing said part on said second side with an infrared radiometer which tracks the moving heating spot on said second side after a sufficient delay to permit heat to pass through said part to said second side, to detect the heat transmitted through said part as a change in infrared levels obtained and
    c) comparing said change in infrared levels obtained to a known data base of said levels from calibrated porosity samples or a curve of said data base, to quantify the porosity of a plurality of points on said part.

2. The method of claim 1 wherein the heat applied to said part is by a laser beam and said part is a composite part.

3. The method of claim 2 wherein said laser beam is controlled as to intensity and duration by a computer.

4. The method of claim 3 wherein said laser beam is divergent and moves as a laser spot across a portion of said part on said first side and said infrared radiometer views the part on said second side and tracks the moving laser spot on said second side after said delay.

5. The method of claim 3 wherein said part is of complex geometry and is moved across said laser beam, said infrared radiometer being directed at said second side at an angle $\theta$, offset from said laser beam so as to allow for said delay in detecting the heat transmitted through said part.

6. The method of claim 5 wherein said laser beam is controlled by said computer for duration, strength and frequency of said laser beam emission and said infrared radiometer is monitored by said computer for collection of said change of infrared levels therefrom.

7. An apparatus for quantifying porosity of a nonmetallic part having a first side and a second side substantially opposite said first side comprising:
    a) means for directing a gas jet or laser beam at said first side as a relatively moving heating spot thereon, to transmit heat through said part to said second side,
    b) an infrared radiometer (IR) directed at said second side, which tracks said moving heating spot on said second side after a sufficient delay to permit heat to pass through said part to said second side, to detect the heat transmitted through said part as a change in infrared levels obtained and
    c) means for comparing said change in infrared levels obtained to a known data base of said levels from calibrated porosity samples or a curve of said data base, to quantify the porosity of a plurality of points on said part.

8. The apparatus of claim 7 wherein said IR is directed at said second side at an angle $\theta$ with the incoming laser beam and means for rotating said part between said laser beam and said IR across said angle $\theta$, to allow for said delay in detecting the heat transmitted through said part.

9. The apparatus of claim 8 wherein said laser beam is controlled by a computer as to duration, frequency and strength of said laser beam and said IR is controlled by said computer as to its angle $\theta$ and as to storing of heat transmitted data of thermal values transmitted through said part from said laser beam.

10. A method for quantifying porosity of a non-metallic part having a first side and a second side substantially opposite said first side comprising:
    a) applying heat to said first side by a laser beam which relatively moves as a laser spot across a portion of said first side,
    b) viewing said part on said second side with an infrared radiometer which tracks the moving laser spot on said second side after a sufficient delay to permit heat to pass through said part to said second side, to detect the heat transmitted through said part as a change in infrared levels obtained and
    c) comparing said change in infrared levels obtained to a known data base of said levels from calibrated porosity samples or a curve of said data base, to quantify the porosity of a plurality of points on said part.

11. The method of claim 10 wherein said part is of complex geometry, said part being relatively moved across said laser beam, said infrared radiometer being directed at said second side at an angle $\theta$ offset from said laser beam so as to allow for said delay in detecting the heat transmitted through said part.

12. An apparatus for quantifying porosity of a nonmetallic part having a first side and a second side substantially opposite said first side, comprising means for directing a laser beam at said first side to transmit heat through the part to said second side, an infrared radiometer (IR) directed at said second side at an angle $\theta$ with the incoming laser beam, means for rotating said part between said laser beam and said IR across said angle $\theta$ to allow for a delay between heating a spot on said part by said laser beam and the transmission of heat through said part to said second side, means for activating said IR to detect the heat transmitted through said part as a change in infrared levels obtained, and means for comparing said change in infrared levels to a known data base of said levels from calibrated porosity samples or a curve of said data base, to quantify the porosity of a plurality of points on said part.

13. The apparatus of claim 12 wherein said laser beam is controlled by a computer as to duration, frequency and strength of said laser beam and said IR is controlled by said computer as to its angle $\theta$ and as to storing of heat transmitted data of thermal values transmitted through said part from said laser beam.

* * * * *